(12) United States Patent
van den Berg

(10) Patent No.: US 12,198,702 B2
(45) Date of Patent: Jan. 14, 2025

(54) IN-EAR LIVENESS DETECTION FOR VOICE USER INTERFACES

(71) Applicant: JVCKENWOOD Corporation, Yokohama (JP)

(72) Inventor: Jan Jasper van den Berg, London (GB)

(73) Assignee: JVCKENWOOD Corporation, Yokohama (JP)

( * ) Notice: Subject to any disclaimer, the term of this patent is extended or adjusted under 35 U.S.C. 154(b) by 0 days.

(21) Appl. No.: 18/325,873

(22) Filed: May 30, 2023

(65) Prior Publication Data

US 2023/0306971 A1 Sep. 28, 2023

Related U.S. Application Data

(63) Continuation of application No. 17/087,231, filed on Nov. 2, 2020, now Pat. No. 11,699,449.

(Continued)

(51) Int. Cl.
*G10L 17/24* (2013.01)
*A61B 5/00* (2006.01)
(Continued)

(52) U.S. Cl.
CPC ............ *G10L 17/24* (2013.01); *A61B 5/1076* (2013.01); *A61B 5/117* (2013.01); *A61B 5/6817* (2013.01); *G06F 16/636* (2019.01); *G06F 21/32* (2013.01); *G06Q 20/40145* (2013.01); *G06V 40/1365* (2022.01); *G06V 40/197* (2022.01);
(Continued)

(58) Field of Classification Search
CPC ......... G10L 17/24; G10L 17/04; G10L 17/06; G10L 17/10; G10L 25/51; A61B 5/1076; A61B 5/117; A61B 5/6817; A61B 2503/12; A61B 5/0077; A61B 5/1075; A61B 5/1077; A61B 5/1079; A61B 5/1171; A61B 5/4803; G06F 16/636; G06F 21/32;
(Continued)

(56) References Cited

U.S. PATENT DOCUMENTS 5,787,187 A * 7/1998 Bouchard ............... A61B 5/12
235/382
9,013,701 B2 4/2015 Hart et al.
(Continued)

FOREIGN PATENT DOCUMENTS

| CN | 107450432 A | 12/2017 | |
|---|---|---|---|
| GB | 2588958 A * | 5/2021 | ............. G06F 1/163 |
| JP | 2016-013343 A | 1/2016 | |

OTHER PUBLICATIONS

"International Search Report and Written Opinion mailed on Jun. 21, 2020 for PCT Application No. PCT/JP2021/010439", 12 pages.

(Continued)

*Primary Examiner* — Linda Wong
(74) *Attorney, Agent, or Firm* — Perkins Coie LLP; Han-Wei Chen; Andrew T. Pettit

(57) ABSTRACT

Introduced here are approaches to authenticating the identity of speakers based on the "liveness" of the input. To prevent spoofing, an authentication platform may establish the likelihood that a voice sample represents a recording of word(s) uttered by a speaker whose identity is to be authenticated and then, based on the likelihood, determine whether to authenticate the speaker.

13 Claims, 12 Drawing Sheets

Related U.S. Application Data

(60) Provisional application No. 63/002,051, filed on Mar. 30, 2020.

(51) Int. Cl.
| | |
|---|---|
| *A61B 5/107* | (2006.01) |
| *A61B 5/117* | (2016.01) |
| *G06F 16/635* | (2019.01) |
| *G06F 21/32* | (2013.01) |
| *G06Q 20/40* | (2012.01) |
| *G06V 40/12* | (2022.01) |
| *G06V 40/18* | (2022.01) |
| *G06V 40/70* | (2022.01) |
| *G10L 17/04* | (2013.01) |
| *G10L 17/06* | (2013.01) |
| *G16H 50/50* | (2018.01) |

(52) U.S. Cl.
CPC .............. *G06V 40/70* (2022.01); *G10L 17/04* (2013.01); *G10L 17/06* (2013.01); *G16H 50/50* (2018.01)

(58) Field of Classification Search
CPC ......... G06Q 20/40145; G06V 40/1365; G06V 40/197; G06V 40/70; G06V 40/40; G16H 50/50

See application file for complete search history.

(56) References Cited

U.S. PATENT DOCUMENTS

| | | |
|---|---|---|
| 2010/0075631 A1 | 3/2010 | Black et al. |
| 2019/0012444 A1 | 1/2019 | Lesso et al. |
| 2019/0012445 A1 | 1/2019 | Lesso et al. |
| 2019/0289409 A1* | 9/2019 | Greenberg ............. A61B 5/125 |
| 2020/0074055 A1* | 3/2020 | Lesso ..................... G10L 17/10 |

OTHER PUBLICATIONS

Wang, et al., Wang et al., EarDynamic: An Ear Canal Deformation based Continuous User Authentication using in-ear wearables, 2021 (Year: 2021).

\* cited by examiner

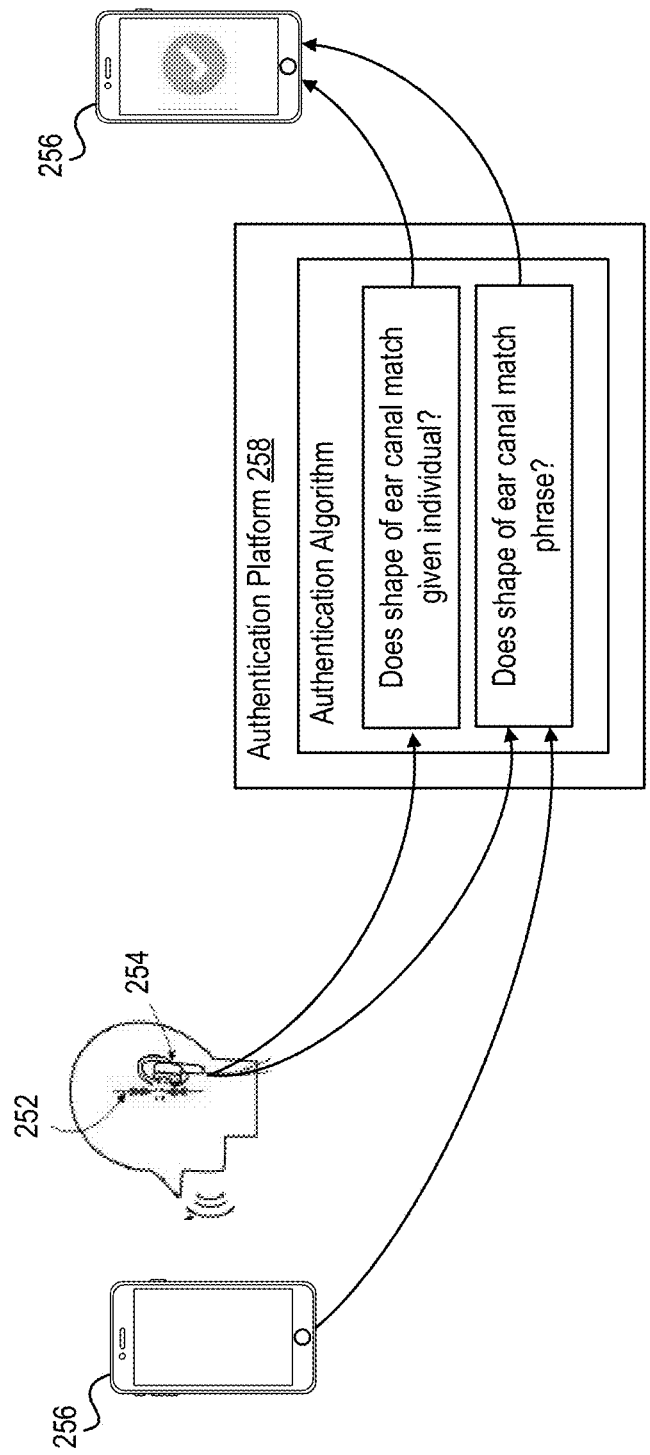

IN-EAR LIVENESS DETECTION FOR VOICE USER INTERFACES

CROSS-REFERENCE TO RELATED APPLICATIONS

This application is a continuation of U.S. application Ser. No. 17/087,231, titled "In-Ear Liveness Detection for Voice User Interfaces" and filed Nov. 2, 2020, which claims priority to U.S. Provisional Application No. 63/002,051, titled "In-Ear Liveness Detection for Voice Interfaces" and filed on Mar. 30, 2020, which are incorporated by reference herein in their entireties.

TECHNICAL FIELD

The present disclosure pertains to biometric authentication in computer security and, more specifically, to techniques on enhancing the security of voice authentication based on one or more correlated physiological characteristics.

BACKGROUND

Biometric authentication procedures verify the identity of an individual through unique biometric characteristics. These biometric characteristics are more difficult to spoof and more convenient since the corresponding individuals do not have to remember passwords or manage tokens. Instead, the authenticator is part of the individual.

Voice recognition (also referred to as "voice authentication") involves analysis of a voice sample to verify the identity of the speaker. Various physiological features, such as the shape of the mouth, airway, and soft-tissue cavities, influence voice patterns in such a manner that a unique vocal profile can be created for each individual. This vocal profile may be referred to as a "vocal fingerprint" or "voiceprint."

There are two main approaches to voice authentication, namely, the text-independent approach and the text-dependent approach. In the text-independent approach, voice authentication can be performed using any passphrase. In the text-dependent approach, voice authentication requires that the same passphrase be used for enrollment and verification. This means that a speaker will be asked to utter a predetermined phrase for authentication purposes. However, with the prevalence of artificial intelligence-drive (AI-driven) technologies, both traditional text-independent and text-dependent approaches are subject to spoofing.

BRIEF DESCRIPTION OF THE DRAWINGS

FIG. 2B illustrates a schematic implementation of the system of FIG. 2A.

Figure 1:
FIG. 1 includes a high-level illustration of a conventional authentication procedure in which an unknown speaker is prompted to utter a passphrase by an electronic device that generates a recording of the uttered passphrase in the form of analog audio data.

Various features of the technologies described herein will become more apparent to those skilled in the art from a study of the Detailed Description in conjunction with the drawings. Embodiments are illustrated by way of example and not limitation in the drawings, in which like references may indicate similar elements. While the drawings depict various embodiments for the purpose of illustration, those skilled in the art will recognize that alternative embodiments may be employed without departing from the principles of the technologies. Accordingly, while specific embodiments are shown in the drawings, the technology is amenable to various modifications.

DETAILED DESCRIPTION

To enroll in an authentication program, an individual (also referred to as a "user") may initially be prompted to provide a voice sample that is used to create a reference template against which future voice samples are compared for authentication purposes. At a high level, the reference template is representative of vocal qualities, such as duration, intensity, dynamics, pitch, and the like, that are determined from the voice sample.

FIG. 1 includes a high-level illustration of a conventional authentication procedure in which an unknown speaker is prompted to utter a passphrase by an electronic device that generates a recording of the uttered passphrase in the form of analog audio data. Examples of electronic devices include mobile phones, tablet computers, and point-of-sale (POS) systems. Thereafter, the analog audio data can be converted into a digital representation (e.g., in the frequency spectrum). This could be done by the electronic device or another electronic device (e.g., a computer server) to which the electronic device is communicatively connected. By analyzing the digital representation of the analog audio data, features and/or patterns can be identified that are representative of the unknown speaker.

Generally, these features and/or patterns are compared to one or more reference templates in order to establish the identity of the unknown speaker. For example, if the unknown speaker is attempting to verify her identity as a given individual by providing a voice sample, then the voice sample can be compared to the reference template that was previously created for the given individual. If the voice sample matches the reference template, then the unknown speaker may be authenticated as the given individual. However, if the voice sample does not match the reference template, then the electronic device may determine that the unknown speaker has not successfully verified her identity.

Such s technique is susceptible to spoofing, however, regardless of the approach to voice authentication that is employed. With respect to the text-dependent approach, if an unauthorized individual (also referred to as a "spoofer") has access to a recording of the impersonated individual uttering the passphrase, then the spoofer may simply initiate playback of the recording. While the text-independent approach is considered more secure against playback attacks, AI-driven generator programs able to create voice samples pose a security risk. With enough voice samples of a given individual, an AI-driven generator program may be able to generate a new, completely fictional voice sample that is very realistic.

Introduced here, therefore, are approaches to authenticating the identity of speakers based on the "liveness" of the input. To prevent spoofing, an authentication platform may establish the likelihood that a voice sample represents a recording of word(s) uttered by a speaker whose identity is to be authenticated and then, based on the likelihood, determine whether to authenticate the speaker. More specifically, the authentication platform may generate a "liveness signal" that is indicative of a biometric characteristic that can be used to establish whether the speaker actually uttered the passphrase. Ideally, the biometric characteristic should be unique to the speaker, unique to the passphrase, or difficult to infer/guess.

The outer ear (also referred to as the "auricle" or "pinna") is an attractive option for authorization as the auricle and ear canal are nearly fully formed when a person is born and remain substantially the same shape throughout that person's lifetime. The shape of the ear canal may be thought of as a unique biometric that can be measured, for example, through reflections of a probing signal that are detected by a microphone. This biometric can be used in several different ways.

First, an authentication platform may look at deformation of the ear canal as proof that a voice sample is provided by the speaker. Assume, for example, that a speaker wearing an electronic device in the auricle is prompted to utter a passphrase for authentication. In such a scenario, the electronic device can emit a probing signal into the ear canal and then generate data that is representative of the probing signal as reflected by the ear canal. By comparing the data to a voice sample indicative of a recording of the passphrase, the authentication platform can establish the likelihood that the speaker actually uttered the passphrase. More specifically, the authentication platform can examine a portion of the data that corresponds to the utterance of the passphrase to determine whether that data indicates the ear canal deformed as would be expected while speaking.

Second, an authentication platform may utilize the deformation itself for the purpose of authentication. As mentioned above, when a speaker moves her jaw, the ear canal will deform in a detectable manner. Because the ear canal itself represents a unique biometric, deformation of the ear canal can also represent a unique biometric. Historically, individuals may have been prompted to utter several passphrases during registration so that multiple reference templates could be created and the same passphrase is not used for each authentication. A similar approach could be employed here. However, instead of converting the voice samples provided during registration into reference templates, the authentication platform may general models indicative of deformation of the ear canal as different passphrases are uttered. Then, when a speaker is prompted to utter a passphrase for authentication as a given individual, the authentication platform can determine whether the shape of the ear canal as the speaker utters the passphrase matches the model that is associated with the given individual and passphrase.

For the purpose of illustration, embodiments may be described in the context of an individual who audibly utters a passphrase that is detectable, for example, by a microphone. Note, however, that deformation of the ear canal will occur regardless of whether sound is actually emitted from the mouth of the individual. Thus, the term "utter," as used herein, may refer to an audible vocalization or an inaudible vocalization. Rather than audible utter a passphrase, some situations (e.g., crowded stores) may be better suited for inaudibly uttering or "lip syncing" the passphrase.

Although not required, implementations are described below in the context of computer-executable instructions, such as routines executed by a general-purpose electronic device such as a computer server, POS system, tablet computer, or mobile phone. Indeed, the term "electronic device" is generally used interchangeably with the term "computing device," and thus may pertain to computer servers, POS systems, tablet computers, mobile phones, and various other electronic devices such as earphones and hearing aids.

While aspects of the technology, such as certain modules, may be described as being performed exclusively or primarily on a single electronic device, some implementations are practices in distributed environments where modules are shared among multiple electronic devices that are linked through a network, such as a local area network (LAN), wide area network (WAN), or the Internet. For example, a speaker may be prompted to utter a passphrase by a mobile application executing on a mobile phone, but the recording of the passphrase may be analyzed by an authentication platform that resides on a computer server that is communicatively connected to the mobile phone. In a distributed computing environment, modules can be located in both local and remote memory storage devices.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The term "based on" is also to be construed in an inclusive sense rather than an exclusive or exhaustive sense. Thus, unless otherwise noted, the term "based on" is intended to mean "based at least in part on."

The terms "connected," "coupled," or any variant thereof is intended to include any connection or coupling between two or more elements, either direct or indirect. The connection/coupling can be physical, logical, or a combination thereof. For example, objects may be electrically or communicatively coupled to one another despite not sharing a physical connection.

The term "module" refers broadly to software components, firmware components, and/or hardware components. Modules are typically functional components that generate output(s) based on specified input(s). A computer program may include one or more modules. Thus, a computer program may include multiple modules responsible for completing different tasks or a single module responsible for completing all tasks.

When used in reference to a list of multiple items, the term "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Overview of Liveness Detection for Authentication

Introduced here are authentication platforms that use deformation of the ear canal as biometric proof that a voice sample was actually provided by a speaker. As further discussed below, proof can be collected using a probing signal that is emitted into the ear canal, which is (i) unique to the speaker and (ii) unique to the dynamic deformations caused by speaking. Reflections of the probing signal can be detected by an ear canal shape sensor (or simply "shape sensor") that is positioned proximate to the ear.

An authentication platform can be used to secure biometric-driven transactions such as payments authorized through voice interfaces. Thus, an authentication platform may be configured to authenticate a voice sample based on (i) characteristic features of audio data and/or (ii) a security score associated with a measured characteristic change of the shape of the ear canal that is uniquely tied to the voice sample being authenticated.

Several different approaches to authentication are discussed in greater detail below. These approaches include:
  Passphrase Authentication: Authentication is based on a measured characteristic of ear canal deformation as the speaker utters a fixed passphrase;
  Monitored Speech Authentication: Authentication is based on a measured characteristic of ear canal deformation as the speaker normally interacts with a speech-driven interface or the environment (e.g., conversing with a clerk at a business); and
  Challenge-Response Authentication: Authentication is based on a measured characteristic of ear canal deformation, where the phrase to be authenticated is algorithmically chosen and could be different each time that an authentication procedure is performed.

In some embodiments the authentication platform operates independently to authenticate the identity of speakers, while in other embodiments the authentication platform operates in conjunction with another system. For instance, a payment system may interface with an authentication platform to ensure that payment procedures are completed in a secure manner. As one example, the authentication platform may be involved in facilitating a pay-by-voice payment procedure where the speaker's voice is used to select a product for purchase or confirm a transaction. As another example, the authentication platform may be involved in a "non-voice" payment procedure (e.g., transaction completed via a mobile application, web browser, etc.) where deformation of the ear canal can be used as part of the security protocol. Thus, the approaches described herein may be used in the context of voice-driven applications and applications not driven by voice.

Overview of Authentication Platform

Figure 2A:
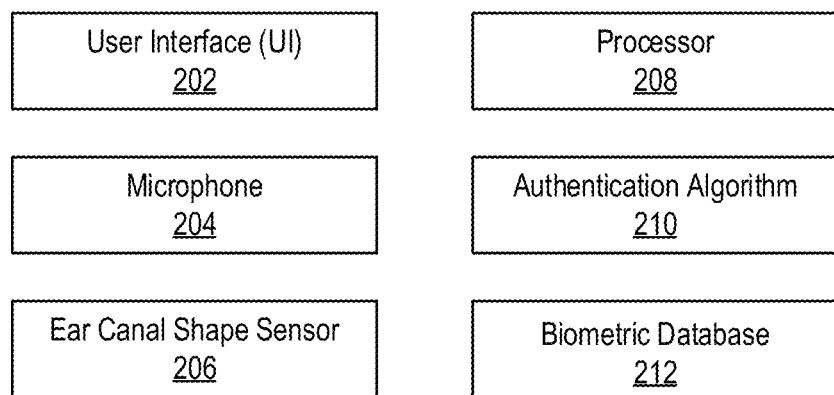
FIG. 2A includes a high-level representation of a system that can be used to authenticate the identity of a speaker.

FIG. 2A includes a high-level representation of a system 200 that can be used to authenticate the identity of a speaker. As shown in FIG. 2A, the system 200 can include a user interface 202, microphone 204, ear canal shape sensor (or simply "shape sensor") 206, processor 208, authentication algorithm 210, and biometric database 212 stored in a memory (not shown). As further discussed below, these elements of the system 200 can be embedded in a single electronic device or distributed amongst multiple electronic devices.

The user interface 202 is representative of the interface through which the speaker is able to interact with the system 200. The user interface 202 could be a speech-driven graphical user interface (GUI) shown on the display of an electronic device. Alternatively, the user interface 202 could be a non-speech-driven GUI shown on the display of an electronic device. In such embodiments, the user interface 202 may visually indicate a phrase to be uttered for authentication purposes.

The microphone 204, meanwhile, is configured to generate audio data that is representative of the sound waves corresponding to a speaker's voice. Assume, for example, that the user interface 202 indicates that the speaker should utter a phrase for authentication. In such a scenario, the microphone 204 can record a voice sample of the uttered phrase. The microphone 204 may also include the necessary analog or digital signal processing elements (e.g., electronic circuits, processing algorithms, etc.) to improve the sound quality, remove noise, or perform more advanced functions such as speech recognition.

As noted above, the microphone 204 is embedded in an electronic device. In some embodiments, the electronic device is associated with the speaker. For example, the microphone 204 may be embedded in an earphone, headphone (e.g., in the headphones itself or a cable connected to the headphones), mobile phone, tablet computer, wearable device, etc. In other embodiments, the electronic device is not associated with the speaker. For example, the microphone 204 may be embedded in a POS system through which the speaker is attempting to complete a transaction.

The shape sensor 206 may be any sensing apparatus able to detect the shape of the ear canal. Ideally, the sensing apparatus should be able to detect shape dimensions with a spatial resolution high enough to be able to distinguish between many different individuals, as well as between different deformations of the ear canal of a single individual caused by movement (e.g., of the jaw) when speaking. In one embodiment, the shape sensor 206 is an active sensing apparatus that includes (i) a signal generator (also referred to as a "sound generator" or "sound source") and (ii) a signal sensor. The signal generator is representative of an element that is able to transmit a probing signal into the ear canal. One example of a signal generator is a vibration generator (e.g., an exciter). Normally, the probing signal is representative of an audio signal, though it may not be audible to the speaker. For example, the signal generator may be configured to generate an inaudible chirp signal with a frequency that increases or decreases over time. Alternatively, the signal generator may be configured to generate audio signals representative of white noise or pink noise, in which case an impulse response may be used to measure the shape of the ear canal. As another example, the signal generator may be configured to generate an ultrasonic signal over an interval of time that is emitted into the ear canal. The interval of time may be based on, for example, a characteristic of the ultrasonic signal, individual, or desired level of authentication. Note that in embodiments where the signal generator of the shape sensor 206 is able to emit sound, the signal generate could also serve as the user interface 202. Meanwhile, the signal sensor (also referred to as a "sound sensor") is representative of an element that is able to collect reflections of the probing signal as reflected by structures in the ear canal. In some embodiments, the shape sensor 206 further includes analog or digital signal processing elements to perform functions such as noise removal, spectral filtering, and the like.

The biometric database 212 may store biometric data that is representative of gathered information representing characteristics of speech that can be used to uniquely identify speakers. As further discussed below with reference to FIGS. 3A-C, the biometric data in the biometric database 212 may vary depending on the approach to authentication employed by the system 200. For example, the biometric database 212 may include models indicative of deformation of ear canals when different phrases are uttered by the same individual or different individuals. Each model may be representative of a series of discrete positions indicating how the shape of the ear canal of the corresponding individual changed over time as the corresponding phrase was uttered. These models may be stored in profiles associated with different individuals. A profile could include a single model associated with a single phrase, multiple models associated with a single phrase, or multiple models associated with different phrases.

When executed by the processor 208, the authentication algorithm 210 can obtain as input various data recorded from the individual during the authentication procedure, compare this data to the corresponding data in the biometric database 212, and then output a security score based on the comparison. The security score may be representative of a number, word, or phrase indicating the outcome of the authentication procedure as performed by the authentication algorithm 210. Thus, the security score may represent the certainty with which the system 200 is able to link the input data to the biometric data stored in the biometric database 212. As further discussed with reference to FIGS. 3A-C, the authentication algorithm 210 may operate based on different principles depending on the approach to authentication.

In some embodiments, the elements of the system 200 are embedded in a single electronic device. For example, all elements of the system 200 may be embedded in an electronic device that can be worn in, or held proximate to, the auricle. Such a device (referred to as an "in-ear device") may have the necessary sensors, processing capabilities, and memory stores for implementing the approaches described herein. Examples of in-ear devices include earphones and hearing aids.

In other embodiments, the elements of the system 200 are distributed across multiple electronic devices. For example, some elements of the system 200 may be embedded in a first electronic device that can be worn by the speaker in the auricle, while other elements of the system 200 may be embedded in a second electronic device. The second electronic device may be, for example, a mobile phone, tablet computer, POS system, or computer server. The second electronic device may be responsible for prompting the speaker to utter a phrase and then recording audio data that is representative of the uttered phrase. Additionally or alternatively, the second electronic device may be responsible for analyzing audio data representative of the uttered phrase and/or shape data representative from which deformation of the ear canal can be determined.

FIG. 2B illustrates a schematic implementation of the system of FIG. 2A. Initially, an electronic device can instruct an unknown speaker 252 to utter a phrase for authentication via a user interface. The electronic device may be an electronic device 254 that is worn by the unknown speaker 252 in the auricle, or the electronic device may be another electronic device 256 located proximate to the unknown speaker 252. Electronic device 256 could be, for example, a mobile phone associated with the unknown speaker 252 or a POS system associated with a merchant with which the unknown speaker 252 is attempting to complete a transaction.

As the unknown speaker 252 utters the phrase, two types of data can be generated, audio data and shape data. As discussed above, the shape data may indicate deformation of the ear canal as the phrase is uttered, while the audio data may be representative of a recording of the uttered phrase. As shown in FIG. 2B, the shape data can be generated by electronic device 254 that is worn by the unknown speaker 252 in the auricle. Meanwhile, the audio data could be generated by electronic device 254 worn in the auricle or electronic device 256 located proximate to the unknown speaker 252. Thus, the audio and shape data could be generated by the same electronic device or different electronic devices.

Thereafter, an authentication platform 258 can examine the audio data and/or shape data to determine whether to authenticate the unknown speaker 252 as a given individual. In particular, the authentication platform 258 can implement an authentication algorithm 258 that is designed to produce a security score based on (i) whether the shape of the ear canal as determined from the shape data matches a profile created for the given individual or (ii) whether the shape of the ear canal as determined from the shape data matches the utterance of the phrase as determined from the audio data. As further discussed below, the authentication platform 258 may be implemented on electronic device 254 located in the auricle or electronic device 256 located proximate to the unknown speaker 252. Alternatively, the authentication platform 258 could be implemented entirely on some other electronic device (e.g., a computer server that is communicatively connected to electronic device 254 and/or electronic device 256).

After determining whether the unknown speaker 252 should be authenticated as the given individual who she claims to be, the authentication platform 258 may generate a notification that indicates the authentication status. Here, the notification is presented on electronic device 256 to visually indicate that authentication was completed successfully. However, the notification could be presented by electronic device 254, in which case the notification may audible indicate that authentication was completed successfully. In some embodiments, the unknown speaker 252 may not be explicitly notified that authentication was completed successfully. For example, if the unknown speaker 252 is attempting to complete a transaction with a merchant on electronic device 256 for which authentication is required, the authentication platform 258 may transmit the notification to a payment processor responsible for facilitating transactions on behalf of the merchant.

While the electronic device 254 may be said to be located "in the auricle," only a portion of the electronic device 254 may actually be located in the auricle. For example, a portion of the electronic device 254 may be located in the auricle, while the remainder of the electronic device 254 may be located outside of the auricle. Alternatively, the entire electronic device 254 may be located in the auricle, as is the case with some earphones and hearing aids. In other embodiments, the electronic device 254 is positioned proximate to the auricle rather than in the auricle. For example, the unknown speaker 252 may opt to hold an electronic device adjacent to the auricle as authentication is performed.

Figure 3A:
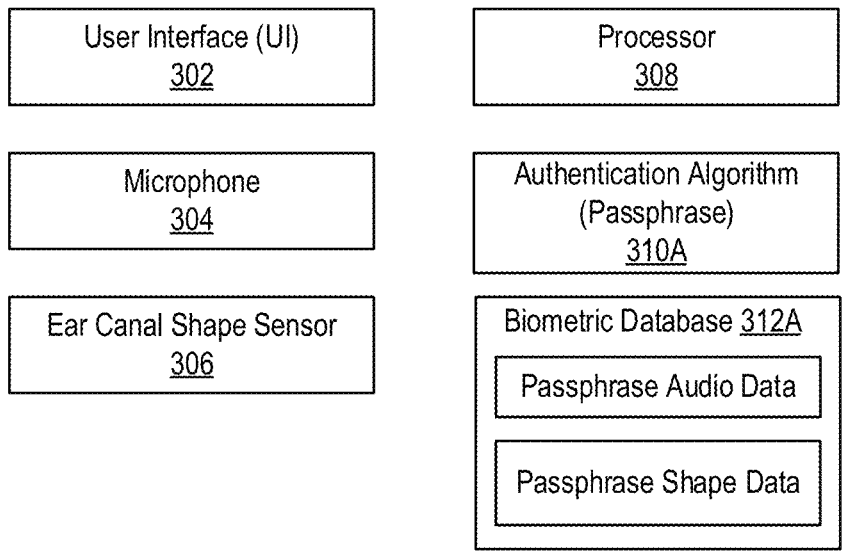
FIG. 3A includes a high-level representation of a system designed for passphrase authentication.
Figure 3B:
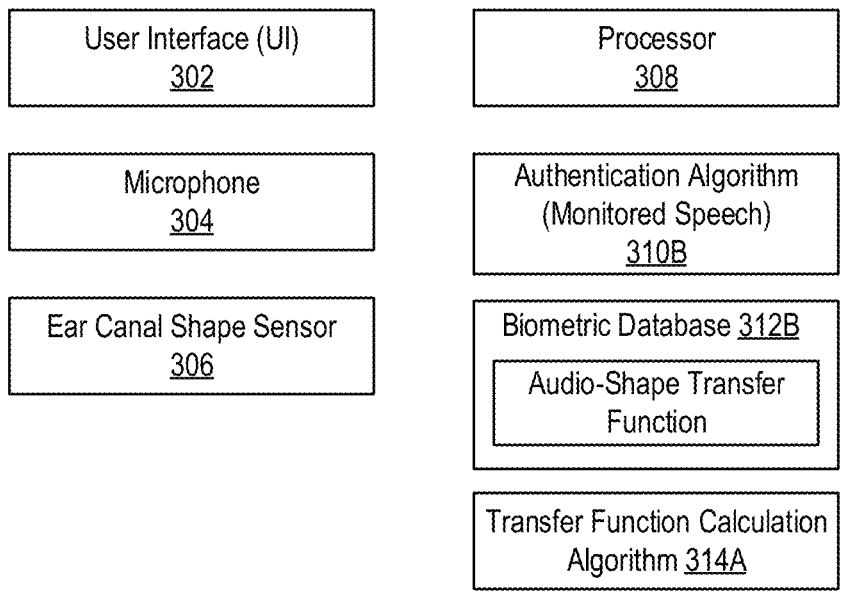
FIG. 3B includes a high-level representation of a system designed for monitored speech authentication.
Figure 3C:
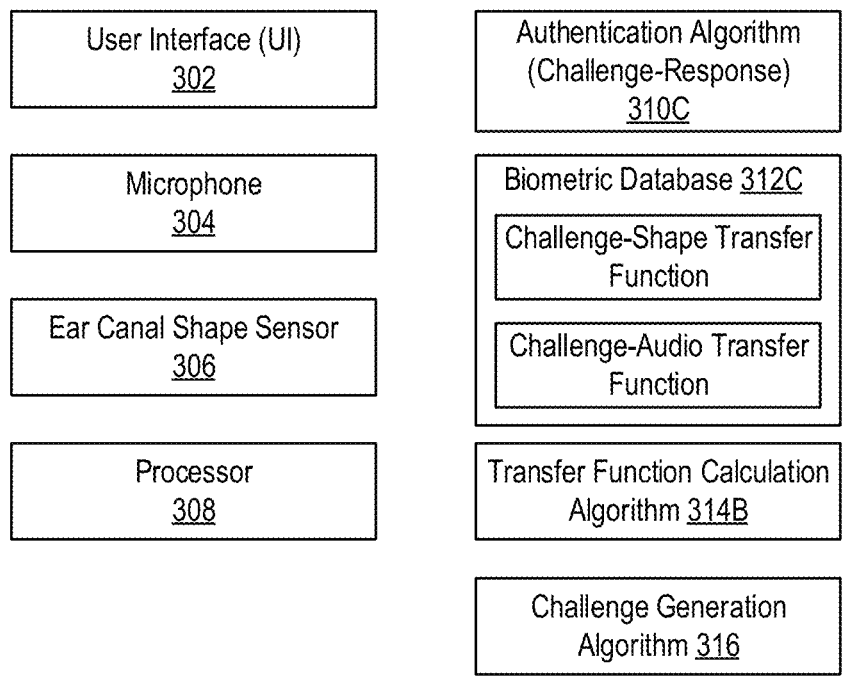
FIG. 3C includes a high-level representation of a system designed for challenge-response authentication.

FIGS. 3A-C include high-level representations of variations of the system 200 shown in FIG. 2A that have been designed for specific approaches to authentication. Each of these variations is described in greater detail below.

FIG. 3A includes a high-level representation of a system 300A designed for passphrase authentication. As shown in FIG. 3A, the system 300A can include a user interface 302, microphone 304, shape sensor 306, and processor 308 similar to the system 200 of FIG. 2A. Here, however, authentication is performed based on a passphrase. The term "passphrase," as used herein, means a phrase that is used as the basis for speech-based authentication. A passphrase could include a single word, or a passphrase could include multiple words. When the system 300A is designed for passphrase authentication, the biometric database 312A may include several forms of biometric data, namely, passphrase audio data that is representative of information regarding recordings of an individual uttering passphrase(s) and passphrase ear canal shape data (or simply "passphrase shape data") that is representative of information regarding the dynamic readings of the shape sensor 306 as the individual utters those passphrase(s).

When the system 300A is designed for passphrase authentication, the authentication algorithm 310A may be configured to produce a security score for each spoken passphrase. Assume, for example, that an individual is instructed to utter a passphrase and then the system 300A obtains audio data generated by the microphone 304 and shape data generated by the shape sensor 306. In such a scenario, the authentication algorithm 310A may compare the audio data to passphrase audio data stored in the biometric database 312A, compare the shape data to passphrase shape data stored in the biometric database 312A, and then calculate the security score based on these comparisons. For instance, the authentication algorithm 310A may generate the security score based on the level of similarity between the audio data and the passphrase audio data and then determine whether an adjustment is necessary based on the level of similarity between the shape data and the passphrase shape data. As an example, the authentication algorithm 310A may multiple the security score by a factor (e.g., 1.0, 0.8, 0.6) that is determined based on the level of similarity between the shape data and the passphrase shape data. Generally, this ensures that the security score will remain high only if the authentication algorithm 310A determines that the shape data substantially matches the passphrase shape data (and thus, the individual actually uttered the passphrase).

Passphrase authentication provides several advantages over other approaches to authentication. First, the authentication process is robust since the same phrase (or same set of phrases) is used each time that authentication is required. Second, if the passphrase is somehow compromised, it will be difficult for a spoofer to guess the general relationship between the passphrase and shape of the ear canal that serves as the biometric authenticator. And third, it is possible to employ different passphrases for different authentication measures, so the authentication process can be independently used for different applications without leaking biometric authenticators between those applications.

FIG. 3B includes a high-level representation of a system 300B designed for monitored speech authentication. As shown in FIG. 3B, the system 300B can include a user interface 302, microphone 304, shape sensor 306, and processor 308 similar to the system 200 of FIG. 2A. Here, however, authentication is performed based on the general relationship between any given phrase spoken by an individual and the related dynamic shape of the individual's ear canal. This could be the basis for authentication through continuous monitoring as the individual interacts with the user interface 302. In such embodiments, the biometric database 312B may include an audio-shape transfer function that is representative of the above-mentioned relationship. The audio-shape transfer function may be used by the system 300B to predict the shape of the ear canal over time for any given audio recording of speech uttered by the individual. Alternatively, the inverse of the audio-shape transfer function can be used. Said another way, for a given shape of the ear canal, the system 300B may predict the corresponding audio recording of speech uttered by the individual.

When the system 300B is designed for monitored speech authentication, the authentication algorithm 310B may be configured to produce a security score based on audio and shape data recorded as the individual interacts with the user interface 302 or some other device, system, or person. Assume, for example, that an individual is attempting to complete a transaction through a POS system managed by a merchant. In such a scenario, the POS system could record speech uttered by the individual (e.g., while conversing with an employee of the merchant, while commenting on content shown in the POS system). As another example, an earphone worn by the individual could be responsible for recording the uttered speech. In comparison to passphrase authentication, monitored speech authentication represents a more natural option of recording speech uttered by the individual for authentication purposes.

Since predetermined passphrases are not used for monitored speech authentication, an audio-shape transfer function can be used to establish the likelihood that a speaker is the person who she claims to be. Thus, the system 300B may include a transfer function calculation algorithm 314A that, when executed by the processor 308, calculates a transfer function based on a set of training examples. Each training example may be representative of a corresponding set of audio and shape data that together indicate how the shape of the ear canal of a given individual changes as she utters certain word(s). Accordingly, the transfer function calculated by the transfer function calculation algorithm 314A may indicate how audio relates to the shape of the ear canal for a given individual. When audio and shape data for a speaker are subsequently obtained by the system 300S, the audio and shape data can be compared against the transfer function created for the individual who the speaker claims to be to produce the security score.

Monitored speech authentication provides several advantages over other approaches to authentication. First, the authentication process is robust against a repeat attack (also referred to as a "replay attack"), where the biometric authenticator is stolen and then subsequently presented by a spoofer attempting to fool an authentication system, since different phrases are used each time that authentication is required. Second, this approach allows for increased security due to its ability to adapt the monitoring duration. Some scenarios may call for extended monitoring durations (e.g., several minutes in length), while other scenarios may call for short monitoring durations (e.g., several seconds in length). And third, monitoring tends to be non-intrusive since it can be performed as the individual normally interacts with her electronic device and/or surroundings without requiring that the individual specifically initiate an authentication procedure.

FIG. 3C includes a high-level representation of a system 300C designed for challenge-response authentication. As shown in FIG. 3C, the system 300C can include a user interface 302, microphone 304, shape sensor 306, and processor 308 similar to the system 200 of FIG. 2A. Here, however, authentication is performed based on the general relationship between a challenge and a response. The term "challenge," as used herein, refers to an input presented to an individual via the user interface 302, while the term "response," as used herein, refers to the phrase spoken in response/reaction to the input. In such embodiments, the biometric database 312C may include a challenge-shape transfer function that is representative of the general relationship between any challenge and a reading of the dynamic shape of the ear canal as the individual utters the response phrase. Moreover, the biometric database 312C may include a challenge-audio transfer function that is representative of the general relationship between any challenge and an audio recording of the response phrase uttered by the individual.

When the system 300C is designed for challenge-response authentication, the authentication algorithm 310C may be configured to produce a security score based on audio and shape data recorded as the individual utters the response phrase to a given challenge. Much like monitored speech authentication, transfer functions may be used in challenge-response authentication to establish the likelihood that a speaker is the person who she claims to be. Thus, the system 300C may include a transfer function calculation algorithm 314B that, when executed by the processor 308, calculates multiple transfer functions based on a set of training examples. Each training example may be representative of a corresponding set of audio and shape data that together indicate how the shape of the ear canal of a given individual changes as she utters a response phrase. Accordingly, the transfer functions calculated by the transfer function calculation algorithm 314B may include (i) a challenge-shape transfer function that indicates how shape of the ear canal relates to a challenge for a given individual and (ii) a challenge-audio transfer function that indicates how audio relates to the challenge for the given individual. When shape and audio data for a speaker are subsequently obtained by the system 300C, the shape and audio data can be compared against the challenge-shape transfer function and challenge-audio transfer function, respectively, created for the individual who the speaker claims to be to produce the security score.

In some embodiments, the system 300C further includes a challenge generation algorithm 316 that is able to generate the challenge that is subsequently presented to the individual to be authenticated. The challenge generation algorithm 316 may be programmed so that the challenge is different each time that the authentication process is performed (e.g., for a given individual, by a given electronic device, etc.) to increase security. For example, an individual may be presented a different challenge each time that she is to be authenticated. A computing device (e.g., a POS system associated with a merchant) could present the same challenge to different individuals, or a computing device could present a different challenge each time that audio data is to be recorded for authentication purposes. Moreover, the characteristics of the challenge may be adapted by the challenge generation algorithm 316 based on the required level of security. For example, the challenge generation algorithm 316 may require that the response phrase have an increased length or complexity if authentication is sought in a sensitive context (e.g., access of personal or financial information).

Challenge-response authentication provides several advantages over other approaches to authentication. First, the authentication process is robust against a repeat attack because the response phrases used for authentication may be different each time that authentication is required. Second, this approach allows for increased security due to its ability to adapt parameters such as the length and complexity of the response phrase.

Figure 4:
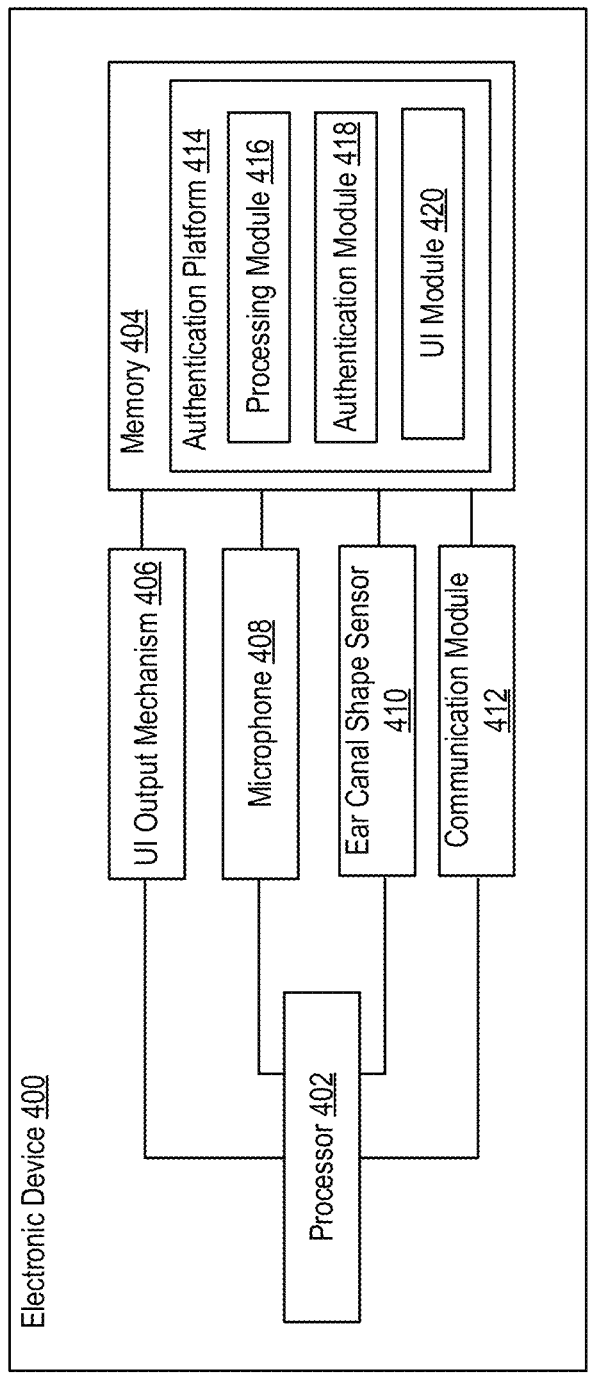
FIG. 4 illustrates an example of an electronic device able to implement an authentication platform that is designed to authenticate the identity of a speaker based on audio data generated by a microphone and shape data generated by a shape sensor.

FIG. 4 illustrates an example of an electronic device 400 able to implement an authentication platform that is designed to authenticate the identity of a speaker based on audio data generated by a microphone 408 and shape data generated by a shape sensor 410. As discussed above, the shape sensor 410 can emit a probing signal into the ear canal and then generate the shape data based on reflections of the probing signal by structures in the ear canal. In some embodiments, the probing signal is an acoustic signal (e.g., a chirp signal), so the shape data may also be audio data in those embodiments.

In some embodiments, the authentication platform 414 is embodied as a computer program that is executed by the electronic device 400. For example, the authentication platform 414 may reside on a headphone or hearing aid that is able to obtain audio and shape data and then determined, based on the audio and shape data, whether to authenticate the speaker. In other embodiments, the authentication platform 414 is embodied as a computer program that is executed by another electronic device to which the electronic device 400 is communicatively connected. In such embodiments, the electronic device 400 may transmit the audio and shape data to the other electronic device for processing. Those skilled in the art will recognize that aspects of the authentication platform could also be distributed amongst multiple electronic devices.

The electronic device 400 can include a processor 402, memory 404, user interface (UI) output mechanism 406, microphone 408, shape sensor 410, and communication module 412. The communication module 412 may be, for example, wireless communication circuitry designed to establish communication channels with other electronic devices. Examples of wireless communication circuitry include integrated circuits (also referred to as "chips") configured for Bluetooth, Wi-Fi, NFC, and the like. The processor 402 can have generic characteristics similar to general-purpose processors, or the processor 402 may be an application-specific integrated circuit (ASIC) that provides control functions to the electronic device 400. As shown in FIG. 4, the processor 402 can be coupled to all components of the electronic device 400, either directly or indirectly, for communication purposes.

The memory 404 may be comprised of any suitable type of storage medium, such as static random-access memory (SRAM), dynamic random-access memory (DRAM), electrically erasable programmable read-only memory (EEPROM), flash memory, or registers. In addition to storing instructions that can be executed by the processor 402, the memory 404 can also store audio data generated by the microphone 408, shape data generated by the shape sensor 410, and data generated by the processor 402 (e.g., when executing the modules of the authentication platform 414). Note that the memory 404 is merely an abstract representation of a storage environment. The memory 404 could be comprised of actual memory chips or modules.

As discussed above, the microphone 408 can be configured to generate audio data that is representative of the sound waves corresponding to a speaker's voice. In some embodiments, the microphone 408 is "always on." Thus, the microphone 408 may continually record audio data regardless of whether an authentication procedure is being performed. In other embodiments, the microphone 408 is activated by the processor 402 responsive to a determination that an authentication procedure is to be performed. For example, the processor 402 may activate the microphone 408 upon determining that the authentication platform 414 has instructed the user interface (UI) module 420 to cause presentation of content via the UI output mechanism 406.

The shape sensor 410 may be any sensing apparatus able to detect the shape of the ear canal. As discussed above, the shape sensor may be configured to transmit a probing signal into the ear canal and then collect reflections of the probing signal as reflected by structures in the ear canal. These reflections may be representative of the shape data from which shape of the ear canal can be determined.

The communication module 412 can manage communications between the components of the electronic device 400. The communication module 412 can also manage communications with other electronic devices. Examples of electronic devices include earphones, headphones, hearing aids, mobile phones, tablet computers, personal computers, and network-accessible server systems comprised of computer server(s). For example, in embodiments where the electronic device 400 is an earphone, the communication module 412 may be communicatively connected to a network-accessible server system that is responsible for examining audio and shape data generated by the microphone 408 and shape sensor 410, respectively.

For convenience, the authentication platform 414 may be referred to as a computer program that resides in the memory 404. However, the authentication platform 414 could be comprised of software, firmware, and/or hardware components implemented in, or accessible to, the electronic device 400. In accordance with embodiments described herein, the authentication platform 414 may include a processing module 416, authentication module 418, and UI module 420. These modules can be an integral part of the authentication platform 414. Alternatively, these modules can be logically separate from the authentication platform 414 but operate "alongside" it. Together, these modules may enable the authentication platform 414 to authenticate the identity of a speaker based on analysis of audio and shape data generated by the microphone 408 and shape sensor 410, respectively.

The processing module 416 may be responsible for applying operations to data obtained by the authentication platform 414. For example, as discussed above, the microphone 408 may generate audio data over time as a speaker is prompted to utter word(s) for the purpose of authentication. The processing module 416 may process (e.g., denoise, filter, or otherwise alter) this audio data so that it is usable by the other modules of the authentication platform 414. Similarly, the processing module 416 may be responsible for processing shape data generated by the shape sensor 410 so that it is usable by the other modules of the authentication platform 414. As an example, the processing module 416 may examine the shape data to remove outlier values and/or form a model representative of deformation of the ear canal over time.

The authentication module 418 may be responsible for implementing the algorithms described herein as needed to implement the various authentication approaches. For example, the authentication module 418 may be configured to execute the authentication algorithms 310A-C, transfer function calculation algorithm 314A-B, or challenge generation algorithm 316 of FIGS. 3A-C. Thus, for each authentication procedure, the authentication module 418 may produce a security score that can be used to determine whether authentication is appropriate based on audio and shape data obtained from the microphone 408 and shape sensor 410, respectively.

Other modules could also be included as part of the authentication platform 414. For example, a UI module 420 may be responsible for generating the content to be output by the UI output mechanism 406 for presentation to the speaker. The form of the content may depend on the nature of the UI output mechanism 406. For example, if the UI output mechanism 406 is a speaker, then the content may include an audible instruction to utter a phrase for authentication purposes. As another example, if the UI output mechanism 406 is a display, then the content may include a visual instruction to utter a phrase for authentication purposes.

Methodologies for Authentication

Figures 5A, 5B:
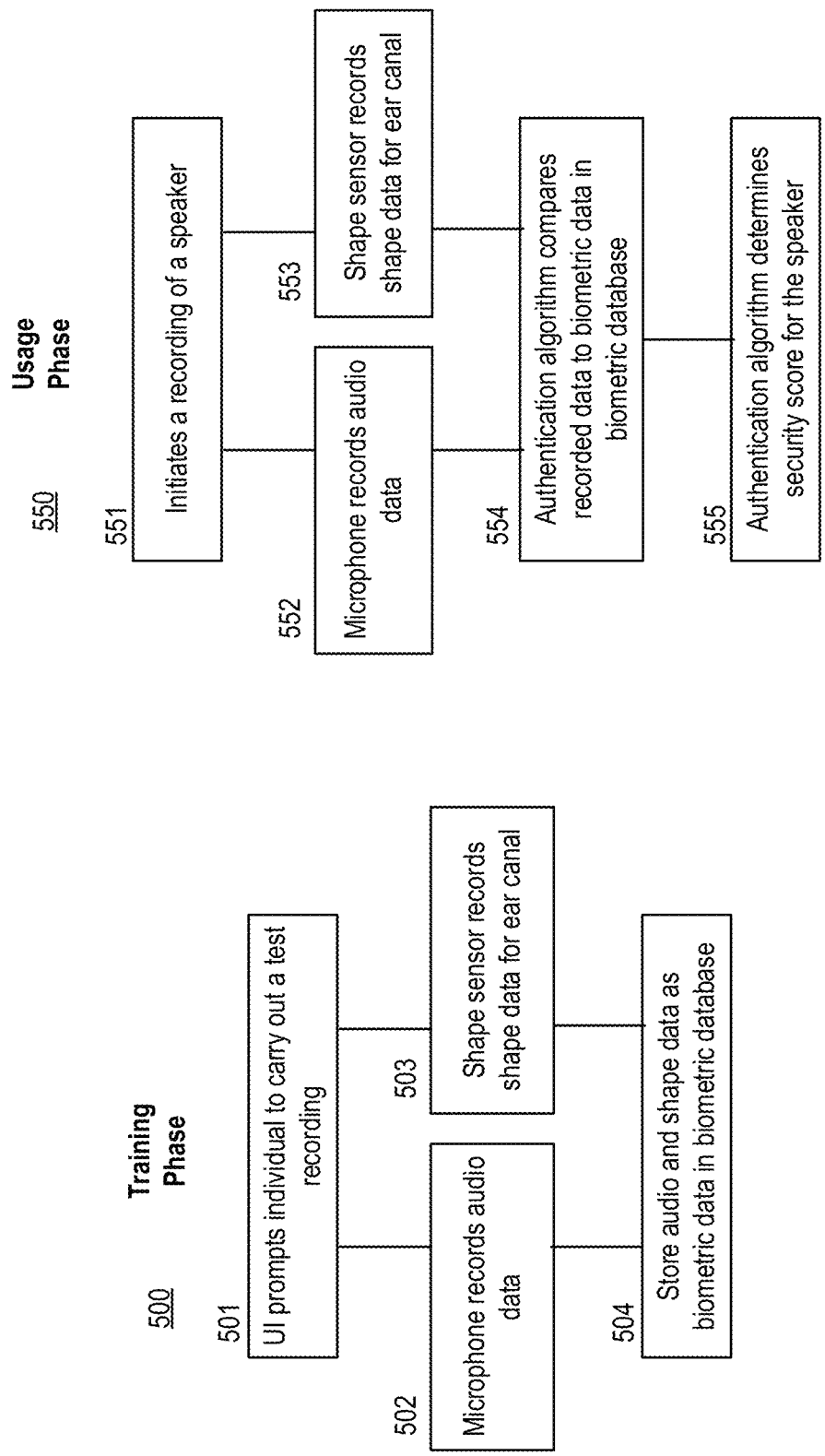
FIGS. 5A-B include flow diagrams of a procedure for authenticating a speaker based on audio data representing a recording of a phrase and shape data representing the shape of the ear canal while the speaker spoke.

FIGS. 5A-B include flow diagrams of a procedure for authenticating a speaker based on audio data representing a recording of a phrase and shape data representing the shape of the ear canal while the speaker spoke. FIGS. 6A-B, 7A-B, and 8A-B include flow diagrams of these processes in the context of passphrase authentication, monitored speech authentication, and challenge-response authentication, respectively. Note that unless otherwise specified, the steps of these processes could be combined with steps of other processes.

As shown in FIGS. 5A-B, the authentication procedure has two phrases, a training phase 500 and a usage phase 550.

In the training phase 500, the user interface may initially prompt an individual to carry out a test recording (step 501). For example, upon indicting an interest in participating in an authentication program, the individual may be requested to complete a registration procedure. As part of the registration procedure, the individual may be requested to utter a phrase comprised of one or more words. The phrase could be a password or some other word depending on the requirements of the authentication program. As the individual utters the phrase, a microphone can record audio data (step 502) and a shape sensor can record shape data (step 503). The audio data may be representative of a recording of some or all of the phrase uttered by the individual, and the shape data may be representative of information regarding shape (and thus deformation) of the ear canal as the phrase was uttered by the individual. Collectively, the audio and shape data may be referred to as the "biometric data" of the individual. At least some of this biometric data can be stored in a biometric database (step 504) so that it can be used in subsequent authentication procedures. As discussed above, the actual content of the biometric database may vary depending on the authentication approach for which the biometric data is to be used.

In the usage phase 550, a recording of a speaker in initiated as part of an authentication procedure (step 551). For example, an electronic device (e.g., electronic device 400 of FIG. 4) may prompt the speaker to utter a phrase in order to authenticate her identity by generating a notification. The notification may be audible, visual, or tactile. As an example, an earphone worn by the speaker in the auricle may issue a verbal command to utter the phrase. As another example, a mobile phone associated with the speaker may issue a visible command to utter the phrase.

As the speaker utters the phrase, a microphone can record audio data (step 552) and a shape sensor can record shape data (step 553). Data may be generated by the microphone and shape sensor as soon as the usage phase 550 of the authentication procedure begins, or data may be generated by the microphone and shape sensor immediately after the electronic device prompts the speaker to utter the phrase.

As discussed above, in some embodiments, neither the microphone nor the shape sensor are embedded in the electronic device that prompts the speaker to utter the phrase. For example, the electronic device may be a mobile phone on which the speaker is attempting to complete a transaction, and the microphone and shape sensor may be embedded within an earphone worn by the speaker in the auricle. In other embodiments, the microphone is embedded in the electronic device but the shape sensor is embedded in another electronic device. Using the above-mentioned example, the microphone may be embedded in the electronic device on which the speaker is attempting to complete the transaction while the shape sensor may be embedded in the earphone. In other embodiments, the microphone and shape sensor are embedded in the electronic device that prompts the speaker to utter the phrase. For example, the microphone and shape sensor may be embedded in an earphone that also prompts the speaker to utter the phrase.

Collectively, the audio and shape data represent the biometric data of the speaker. An authentication algorithm can compare this biometric data (also referred to as "recorded data") to the biometric database (step 554). The comparison may be performed in several ways depending on, for example, the authentication approach. One way involves directly comparing the recorded data of the speaker to the biometric data stored in the biometric database in an attempt to find a matching entry. This option may be employed in the context of passphrase authentication. Alternatively, the recorded data may be compared to predicted biometric data (or simply "predicted data") created using a transfer function stored in the biometric database. This option may be employed in the context of monitored speech authentication or challenge-response authentication.

Moreover, the authentication algorithm can produce a security score (step 555). The security score may be used to determine whether the speaker should be authenticated as a particular individual. Generally, the speaker will be authenticated as the particular individual only if the security score, as determined based on a comparison of the recorded data to the stored biometric data (or simply "stored data") associated with the particular individual, exceeds a threshold.

In some embodiments, the authentication algorithm is configured to calculate the correlation coefficient between either the recorded data and stored data or the recorded data and predicted data. Other metrics may be calculated in addition to, or instead of, the correlation coefficient. These metrics may involve more advanced data analysis and manipulation techniques, such as feature extraction and comparison, spectral analysis, or other mathematics functions that may indicate the similarity between the recorded data and either the stored data or predicted data.

Based on the comparison, the authentication algorithm can calculate the security score that is provided as output. For example, the authentication algorithm may utilize a function or lookup table that indicates the relationship between the metric(s) and the corresponding security score. As an example, assume that the biometric database has stored ten models (also referred to as "instances") indicating deformation of the ear canal as an individual utters a phrase. Recorded data indicating deformation of the ear canal as an unknown speaker utters the same phrase is then compared with these ten models. Such a comparison results in an average correlation coefficient (e.g., 0.992) that is compared to a threshold value (e.g., 0.950). If the average correlation coefficient exceeds the threshold value, then the authentication algorithm may output a security score indicating that the unknown speaker "passed," and thus was authenticated as the individual. However, if the average correlation coefficient does not exceed the threshold value, then the authentication algorithm may output a security score indicating that the unknown speaker "failed," and thus was not authenticated as the individual.

Figures 6A, 6B:
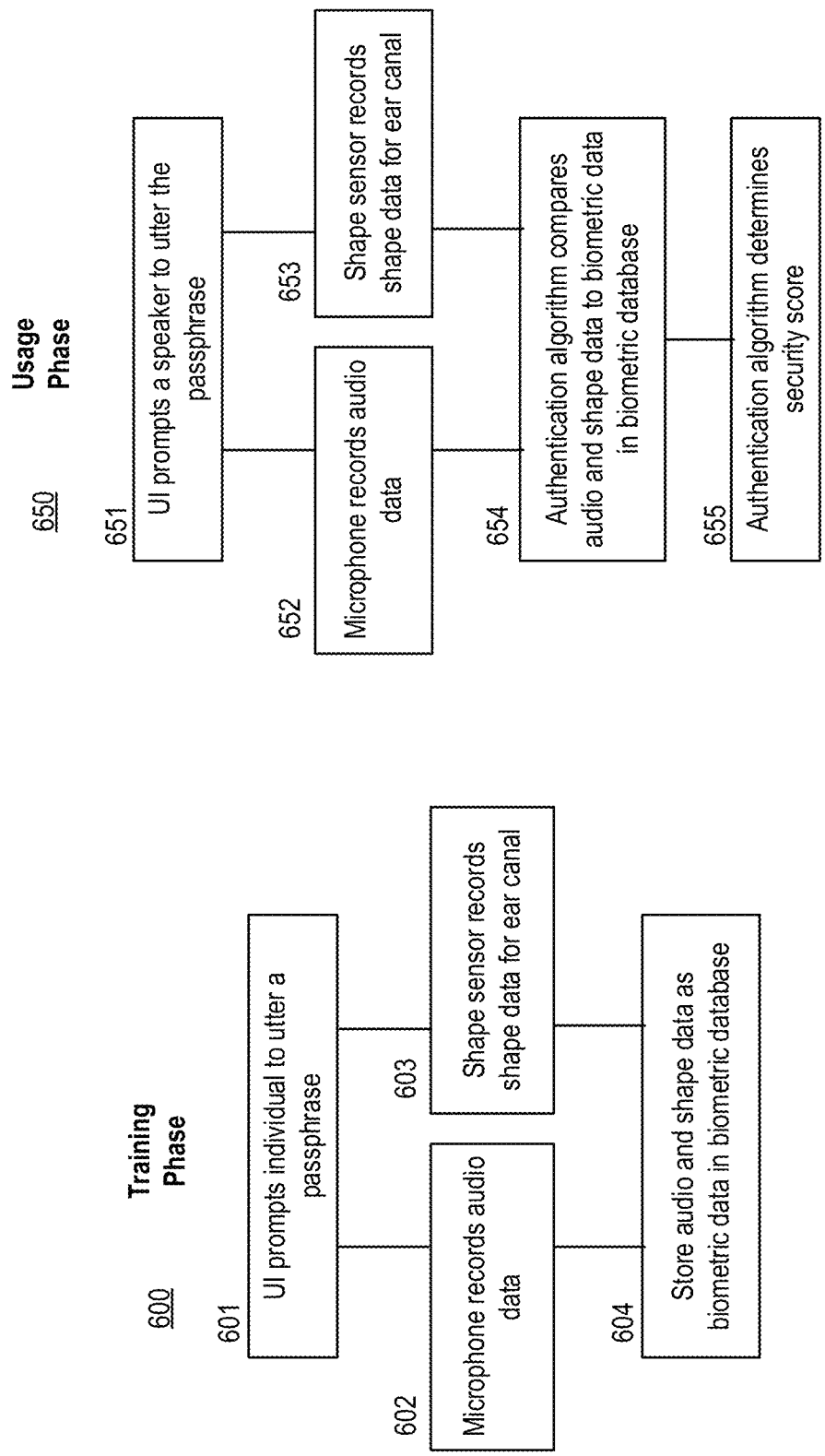
FIG. 6A-B include flow diagrams of the training and usage phases of an authentication procedure performed in accordance with the passphrase authentication approach.

FIGS. 6A-B include flow diagrams of the training and usage phases 600, 650 of an authentication procedure performed in accordance with the passphrase authentication approach. As can be seen in FIGS. 6A-B, the training and usage phases 600, 650 of the authentication procedure may be largely similar to the training and usage phases 500, 550 of FIGS. 5A-B.

In the training phase 600, the user interface may initially prompt an individual to utter a passphrase (step 601). For example, as part of a registration procedure for an authentication program, the individual may be requested to utter a passphrase that will be subsequently used for authentication. The passphrase may be a single word or a collection of words (e.g., a sentence that covers a large pronunciation gamut, includes a large proportion of the alphabet, etc.). Those skilled in the art will recognize that the registration procedure could require that the individual utter the same passphrase multiple times and/or utter different passphrases. Thus, the training phase 600 may be completed multiple times in succession.

As the individual utters the passphrase, a microphone can record audio data (step 602) and a shape sensor can record shape data (step 603). Collectively, the audio and shape data may be referred to as the "biometric data" of the individual. At least some of this biometric data can be stored in a biometric database (step 604) so that it can be used in subsequent authentication procedures. This biometric data may include raw sensor measurements or a representation of those measurements (e.g., values averaged over multiple measurements, compressed data, or features/metrics extracted from those measurements).

In the usage phase 650, a user interface may initially prompt a speaker to utter the passphrase as part of an authentication procedure (step 651). For example, an electronic device (e.g., electronic device 400 of FIG. 4) may prompt the speaker to utter a passphrase in order to authenticate her identity. As the speaker utters the passphrase, a microphone can record audio data (step 652) and a shape sensor can record shape data (step 653). Data may be generated by the microphone and shape sensor as soon as the usage phase 650 of the authentication procedure begins, or data may be generated by the microphone and shape sensor immediately after the electronic device prompts the speaker to utter the passphrase.

Collectively, the audio and shape data represent the biometric data of the speaker. An authentication algorithm can compare this biometric data (also referred to as "recorded data") to the biometric database (step 654). For example, if the speaker is attempting to authenticate her identity as a particular individual, then the authentication algorithm may directly compare the recorded data to biometric data in the biometric database that is associated with the particular individual. Moreover, the authentication algorithm can produce a security score (step 655). The security score may be used to determine whether the speaker should be authenticated as the particular individual. As discussed above, the speaker may be authenticated as the particular individual if the security score exceeds a threshold. The security score may be the correlation coefficient or some other metric.

Figures 7A, 7B:
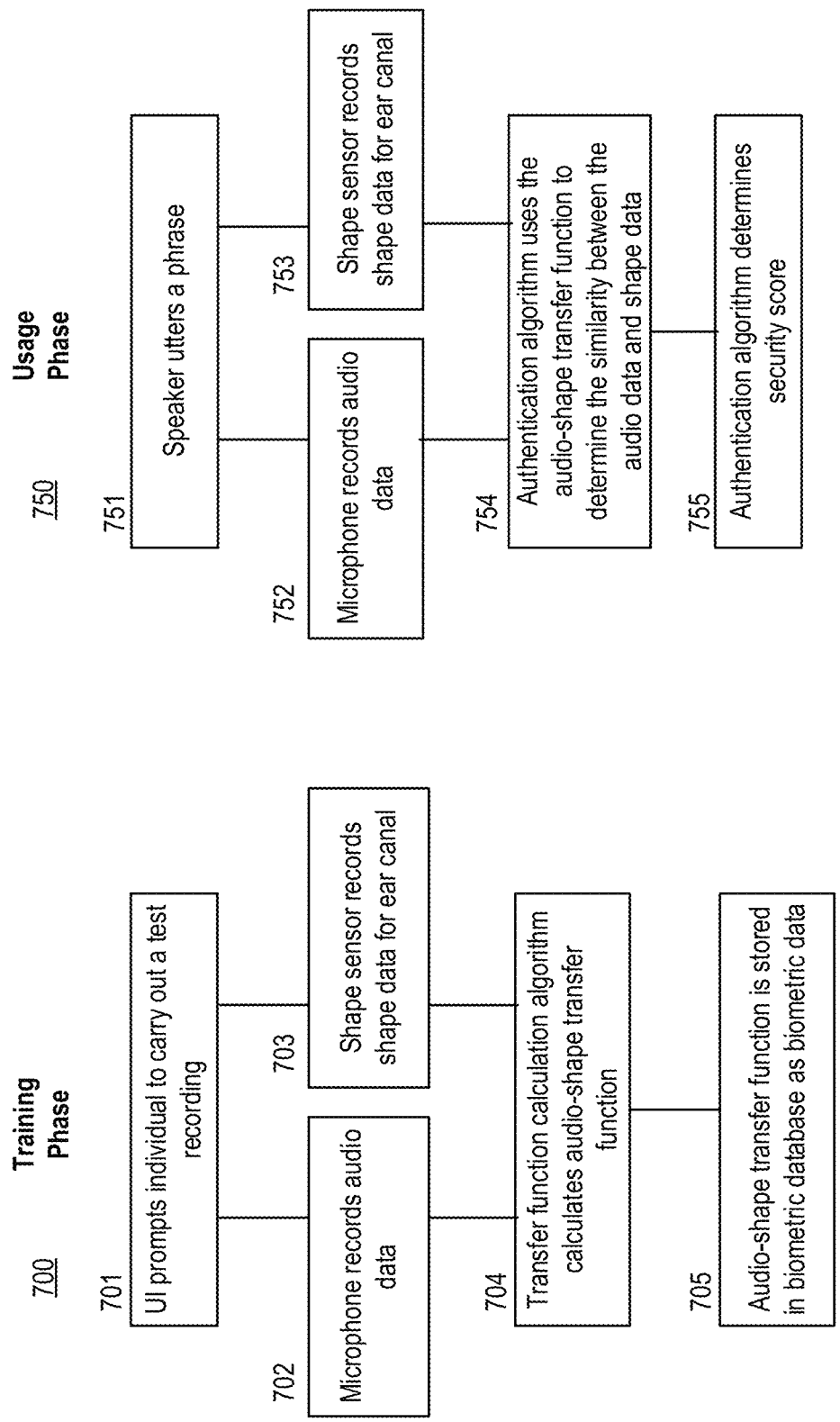
FIGS. 7A-B include flow diagrams of the training and usage phases of an authentication procedure performed in accordance with the monitored speech authentication approach.

FIGS. 7A-B include flow diagrams of the training and usage phases 700, 750 of an authentication procedure performed in accordance with the monitored speech authentication approach.

In the training phase 700, the user interface may initially prompt an individual to carry out a test recording (step 701). For example, as part of a registration procedure for an authentication program, the individual may be prompted to read a selected passage of text, or the individual may be recorded while she naturally interacts with a voice-driven interface or her surroundings (e.g., with some other device, system, or person). Those skilled in the art will recognize that test recordings could last several seconds or minutes, depending on the desired amount of recorded speech. As the individual carries out the test recording, a microphone can record audio data (step 702) and a shape sensor can record shape data (step 703). Collectively, the audio and shape data may be referred to as the "biometric data" of the individual.

A transfer function calculation algorithm can then calculate an audio-shape transfer function based on the audio and shape data (step 704). For example, the transfer function calculation algorithm may obtain as input the audio data associated with a given phrase and then predict the corresponding shape data using an audio-shape transfer function that is representative of a regression model, predictive machine learning (ML) model, or the like. Then, the transfer function calculation algorithm may adapt the variables of the audio-shape transfer function based on the similarity between the predicted shape data and the actual shape data recorded by the shape sensor. At a high level, the transfer function calculation algorithm may alter the variables in an attempt to make the predicted shape data substantially match the recorded shape data. The transfer function calculation algorithm may repeat this process for multiple phrases that collectively define a set. The phrases in the set may be selected based on, for example, variety in detected sound quality, words/letters spoken, tone, speed, etc. The audio-shape transfer function can then be stored in a biometric database as biometric data (step 705).

The usage phase 750 may simply begin with a speaker uttering a phrase (step 751). In contrast to the usage phases 550, 650 of FIGS. 5B and 6B, the speaker may not be prompted to utter a specific phrase. Instead, the phrase may simply be any phrase that is uttered by the speaker as she interacts with an electronic device responsible for facilitating the authentication procedure or her surroundings. As the speaker utters the phrase, a microphone can record audio data (step 752) and a shape sensor can record shape data (step 753). Data may be generated by the microphone and shape sensor as soon as the usage phase 750 of the authentication procedure begins. For example, data may be generated by the microphone and shape sensor responsive to detecting that the speaker has naturally uttered a predetermined word (e.g., "authentication" or "verification") or phrase (e.g., "authentication is necessary"). As another example, data may be generated by the microphone and shape sensor responsive to determining that the speaker is attempting to complete an action that requires authentication.

Collectively, the audio and shape data represent the biometric data of the speaker. An authentication algorithm may use the audio-shape transfer function to determine the similarity between this biometric data (step 754). For example, the authentication algorithm may use the audio-shape transfer function to predict shape data that corresponds to the recorded audio data. Then, the authentication algorithm may determine the similarity between the predicted shape data and the actual shape data recorded by the shape sensor for the speaker. For example, the authentication algorithm may calculate the correlation coefficient or some other similarity metric for the predicted and recorded shape data. Moreover, the authentication algorithm can produce a security score (step 755). The security score may be used to determine whether the speaker should be authenticated as the individual whom she claims to be. If the security score is low and/or has a high degree of uncertainty, then the speaker may continue to be monitored. For example, the usage phase 750 may be performed multiple times over the course of several seconds, minutes, or hours until the authentication algorithm has determined with sufficient certainty whether the speaker should be authenticated.

Figures 8A, 8B:
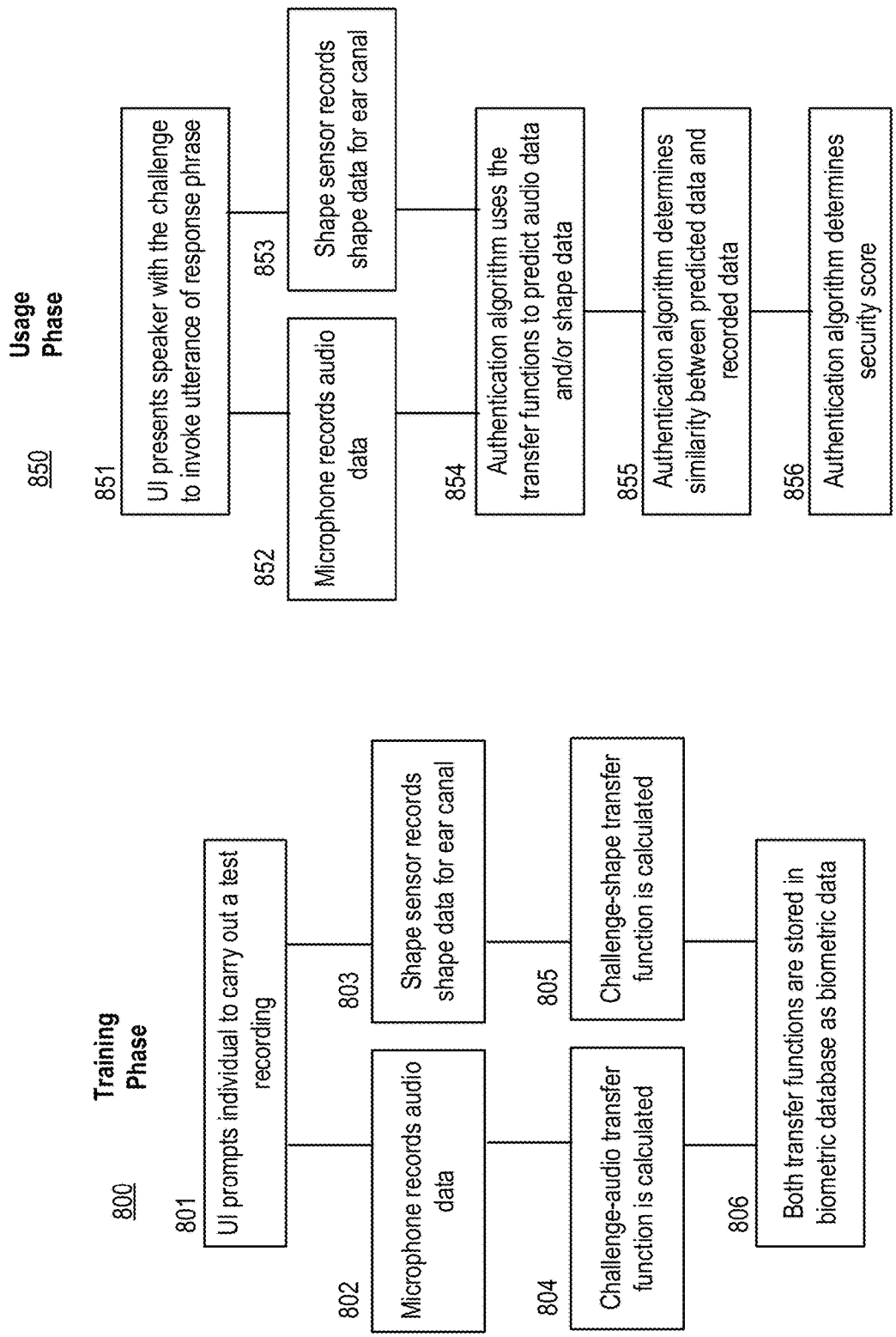
FIGS. 8A-B include flow diagrams of the training and usage phases of an authentication procedure performed in accordance with the challenge-response authentication approach.

FIGS. 8A-B include flow diagrams of the training and usage phases 800, 850 of an authentication procedure performed in accordance with the challenge-response authentication approach.

In the training phase 800, a user interface may initially prompt an individual to carry out a test recording by collecting response phrases to one or more challenges (step 801). For example, as part of a registration procedure for an authentication program, the individual may be requested to respond to a set of challenges created by a challenge generation algorithm (e.g., the challenge generation algorithm 316 of FIG. 3C). As an example, the challenge generation algorithm may randomly select each challenge from a standard database of challenges. As another example, the challenge generation algorithm may determine the required level of security (e.g., for the types of actions to be performed for which authentication is necessary, for the type of authentication approach to be employed) and then choose a challenge from a standard database of challenges that meets those security requirements. Generally, those challenges associated with longer and/or more complex responses phrases are considered more secure (and thus result in more robust authentication). As the individual utters the response phrases, a microphone can record audio data (step 802) and a shape sensor can record shape data (step 803). Collectively, the audio and shape data may be referred to as the "biometric data" of the individual.

A transfer function calculation algorithm can then calculate a challenge-audio transfer function based on the audio data (step 804). Additionally or alternatively, the transfer function calculation algorithm can calculate a challenge-shape transfer function based on the shape data (step 805). These transfer functions may be designed to produce the audio data or shape data for the response phrase for a given challenge. Examples of challenges and their corresponding response phrases include the following:

One or more words are audibly conveyed as the challenge, and the speaker is asked to repeat those word(s);

A numerical equation is visually conveyed as the challenge, and the speaker is requested to utter the answer; and An image of a well-known person or item is visually conveyed as the challenge, and the speaker is quested to identify the person (e.g., by first or last name) or item.

The transfer function calculation algorithm can determine the challenge-audio transfer function and/or challenge-shape transfer function following a similar approach as described for the audio-shape transfer function described above with reference to FIG. 7A. Here, however, the input is the required response phrase while the output is a prediction of either the corresponding audio data or corresponding shape data.

As noted above, a series of challenges may be presented to the individual as part of the training phase 800. Accordingly, the transfer function calculation algorithm may repeat step 804 and/or step 805 for the entire series of challenges. Once completed, all of the transfer functions can be stored in a biometric database as biometric data (step 806).

In the usage phase 850, a user interface may initially present a speaker seeking to authenticate herself as a particular individual with a challenge to invoke an utterance of a corresponding response phrase (step 851). The challenge may be selected by the challenge generation algorithm from a series of challenges completed by the particular individual during the registration process as discussed above. As the speaker utters the response phrase, a microphone can record audio data (step 852) and a shape sensor can record shape data (step 853). Data may be generated by the microphone and shape sensor as soon as the usage phase 850 of the authentication procedure begins, or data may be generated by the microphone and shape sensor immediately after the challenge is presented to the speaker.

Thereafter, an authentication algorithm can use the challenge-audio transfer function and/or challenge-shape transfer function to predict audio data or shape data, respectively, given the challenge presented to the speaker (step 854). The authentication algorithm can predict audio data or shape data following a similar approach as described for the audio-shape transfer function described above with reference to FIG. 7B. Then, the authentication algorithm can determine the similarity between the predicted data and the recorded data (step 855). For example, the authentication algorithm may determine the similarity between predicted audio data output by the challenge-audio transfer function and recorded audio data and/or between predicted shape data output by the challenge-shape transfer function and recorded shape data. Moreover, the authentication algorithm can produce a security score (step 856). The security score may be used to determine whether the speaker should be authenticated as the individual whom she claims to be. If the security score is low and/or has a high degree of uncertainty, then the speaker may be presented another challenge. This other challenge may be more difficult, have different properties, etc.

To increase security, at least some of the steps in FIGS. 6A-B, 7A-B, and 8A-B may be performed in the encrypted domain. For example, all data recording, manipulating, calculating, or storing may be performed in the encrypted domain. Even if not performed in the encrypted domain, these steps may be performed in a secure manner to minimize risk of the authentication process being compromised.

Figure 9:
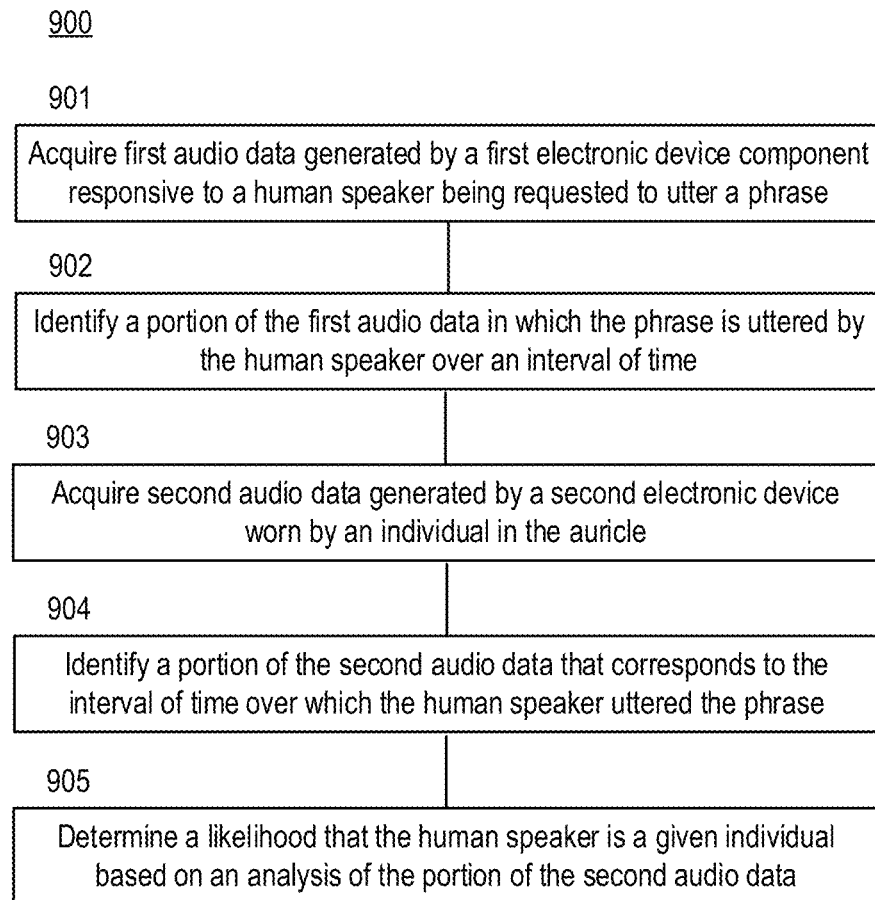
FIG. 9 depicts a flow diagram of a process for biometrically authenticating the identify of a speaker.

FIG. 9 depicts a flow diagram of a process 900 for biometrically authenticating an identity of a human speaker who claims to be a certain individual. Initially, an authentication platform can acquire first audio data that is generated by a first electronic device component responsive to a human speaker being requested to utter a phrase (step 901).

The unknown speaker may be audibly (e.g., through presentation of an audible command) or visibly (e.g., through presentation of a visual command) prompted to utter the phrase. Then, the authentication platform can identify a portion of the first audio data in which the phrase is uttered by the human speaker over an interval of time (step 902). The authentication platform may alter the first audio data to ensure that the relevant portion can be more easily processed. For example, the authentication platform may extract the portion from the first audio data, or the authentication platform may edit (e.g., cut, filter, or otherwise alter) the first audio data.

The authentication platform may also acquire second audio data that is representative of a probing signal as reflected by the ear canal of the human speaker (step 903). The reflections of the probing signal may be detected by a second electronic device component. As discussed above, in some embodiments the first and second electronic device components are part of the same electronic device, while in other embodiments the first and second electronic device components are parts of different electronic devices.

In embodiments where the authentication platform is embodied on an electronic device positioned in the auricle of the human speaker, the authentication platform cause a probing signal to be emitted into the ear canal. Thus, the second electronic device component may emit a probing signal into the ear canal of the human speaker and then record second audio data that is representative of the probing signal as reflected by structures in the ear canal. In some embodiments, the second electronic device component is configured to emit the probing signal into the ear canal responsive to a determination that the unknown speaker has been requested to utter the phrase. Alternatively, the phrase as uttered by the human speaker could act as the probing signal. Thus, the probing signal could be a distinct signal generated by the second electronic device component, or the probing signal could be representative of speech of the human speaker. The authentication platform can then identify a portion of the second audio data that corresponds to the interval of time over which the human speaker uttered the phrase (step 904). Said another way, the authentication platform can identify a portion of the second audio data that temporally corresponds to the portion of the first audio data identified in step 902. For example, the portion of the second audio data may be identified using timestamps in the second audio data. As another example, the portion of the second audio data may be identified using filters (e.g., that indicate the portions of the second audio data where deformation of the ear canal has been detected).

Thereafter, the authentication platform may determine the likelihood that the individual is the human speaker based on an analysis of the portion of the second audio data (step 905). For example, the authentication platform may be configured to establish, based on the portion of the second audio data, a shape of the ear canal over the interval of time. The shape of the ear canal may be represented (and then matched to a biometric database) in several different ways.

In some embodiments, the shape of the ear canal is represented as a profile, such as a shape vector or a simple set of three-dimensional (3D) coordinates at a set resolution, thereby representing the topology of the ear canal. The profile may be representative of the shape of the ear canal as the phrase was uttered. In such embodiments, a comparison may be performed by transforming the topological data associated with a reference biometric (e.g., a reference ear canal) to minimize the mean coordinate positional difference between the reference biometric and the measured ear canal.

Transformations may be necessary to account for variations in position of the electronic device in the auricle at the time that the second audio data was recorded. The minimum mean coordinate difference can then be compared to a predetermined threshold to determine whether the measured ear canal matches the reference biometric. In embodiments where the reference biometrics in the biometric database are highly detailed, the authentication platform may opt against performing a full match against each reference biometric. Instead, the authentication platform can complete initial "pre-matching" using selected coordinates where the highest degree of difference between different reference biometrics (and thus different individuals) is shown. Pre-matching can then be following by a more detailed matching procedure is more than one reference biometric is identified as a candidate.

In some embodiments, the shape of the ear canal is represented entirely in the audio domain. In such embodiments, the physical shape of the ear canal may correspond to an acoustic transfer function of the probing signal. Thus, the "shape" of the ear canal may be stored as a known function that is applied to the frequency and amplitude values of audio data. In its simplest form, the acoustic transfer function indicates what changes occur to a probing signal at various points on a frequency spectrum. An individual's biometric signature could, therefore, be comprised of a set of amplitude transformation values associated with different frequencies. In such embodiments, a mean different score can be calculated for the amplitude and frequency values when comparing the probing signal to a reference biometric.

Moreover, the authentication platform may produce, based on the shape, a security score (or simply "score") indicative of the likelihood that the human speaker is the individual who she claims to be. In some embodiments, this score is compared to a predetermined threshold, and the likelihood that the human speaker is the individual is further based on the comparison. If the score exceeds the threshold, the authentication platform may indicate that the human speaker has been authorized as the individual. However, if the score does not exceed the threshold, the authentication platform may indicate that the human speaker has not been authenticated as the individual.

In some embodiments, the score is produced based on a comparison of the shape of the ear canal to a biometric database to determine whether a matching entry is found. Entries in this biometric database may include reference profiles representing shapes for the ear canal of different persons. Those skilled in the art will recognize that a single person could be associated with multiple reference profiles, for example, one reference profile for the left ear and one reference profile for the right ear. During an authentication procedure, the authentication platform could make use of one or both reference profiles. For example, if authentication is sought in a sensitive context, then the authentication platform may concurrently execute multiple instances of the process 900 so that security scores can be produced for the left and right ears. In such embodiments, the authentication platform may determine whether to authenticate the unknown speaker based on the security score produced for the left ear, the security score produced for the right ear, or both security scores. A similar approach may involve comparing deformation of the ear canal (or a model of the deformation) to the biometric database to determine whether a matching entry is found. Entries in this biometric database may include reference profiles representing deformation of the ear canal as different persons utter the same or different phrases. Additionally or alternatively, the authentication platform may compare the portion of the first audio data to another biometric database to determine whether a matching entry is found. Entries in this biometric database may include reference voice samples for different persons. The authentication platform may be able to determine whether to authenticate the human speaker based on whether matching entries were discovered in any of these biometric databases. For example, the authentication platform may determine the likelihood that the human speaker is the individual who she claims to be based on (i) the matching entry, if any, in the biometric database that includes reference profiles of shapes of ear canals, (ii) the matching entry, if any, in the biometric database that includes reference profiles of deformation of ear canals, and/or (ii) the matching entry, if any, in the biometric database that includes reference voice samples.

Figure 10:
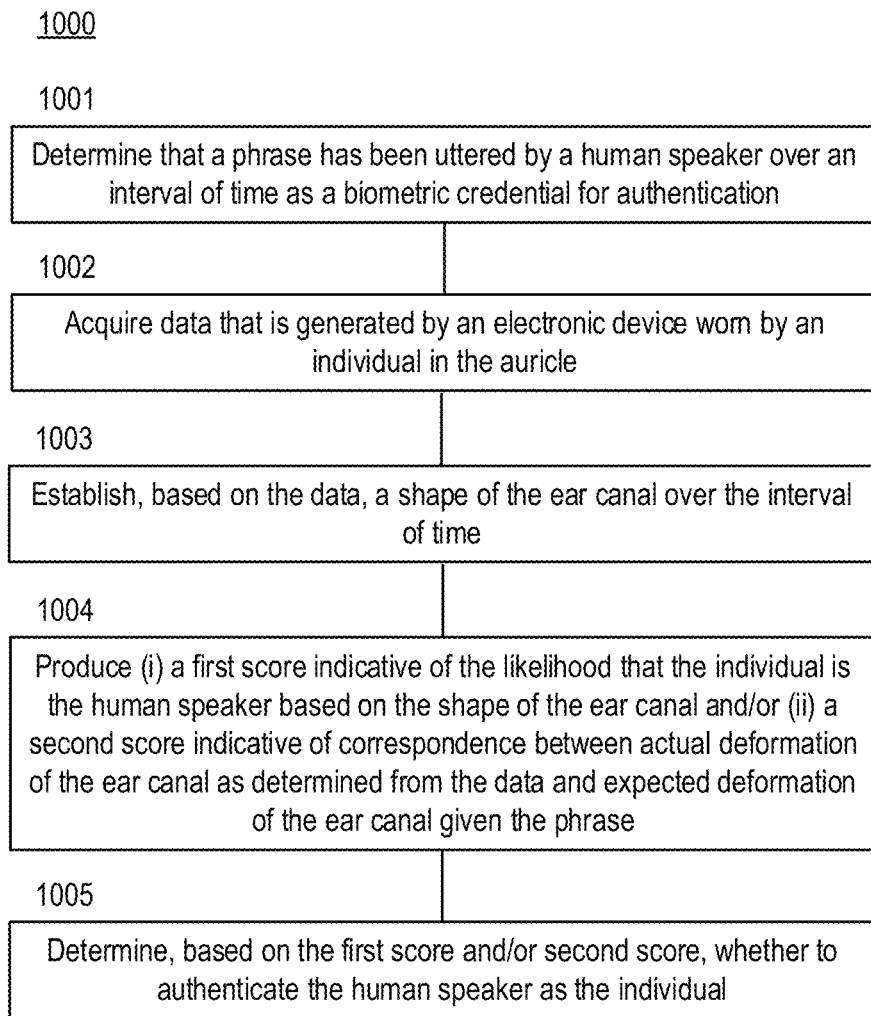
FIG. 10 depicts a flow diagram of a process for determining whether to authenticate the identity of a speaker based on deformation of the ear canal.

FIG. 10 depicts a flow diagram of a process 1000 for determining whether to authenticate the identity of a human speaker based on deformation of the ear canal. Initially, an authentication platform can determine that a phrase has been uttered by a human speaker over an interval of time as a biometric credential for authentication (step 1001). The phrase may be uttered as a means of passphrase authentication, monitored speech authentication, or challenge-response authentication. Then, the authentication platform can acquire shape data (or simply "data") that is generated by an electronic device worn by an individual in the auricle (step 1002). The electronic device may be configured to emit a series of probing signals into the ear canal, and the data may be representative of a series of return signals generated by reflection of the series of probing signals against a surface of the ear canal. In some embodiments, the series of probing signals is representative of a signal with a frequency that increases or decreases over time.

The authentication platform can then establish, based on the data, a shape of the ear canal over the interval of time (step 1003). Moreover, the authentication platform can produce (i) a first score indicative of the likelihood that the individual is the human speaker based on the shape of the ear canal and/or (ii) a second score indicative of correspondence between the actual deformation of the ear canal as determined from the data and expected deformation of the ear canal given the phrase (step 1004). The first score may be produced by examining the data to discover whether the ear canal deformed over the interval as would be expected if the individual were the human speaker. Alternatively, the first score may be produced by determining whether the shape of the ear canal matches an entry in a biometric database that is associated with the individual. Meanwhile, the second score may be produced by applying a transfer function (e.g., an audio-shape transfer function or a challenge-shape transfer function) that predicts the expected deformation given the phrase.

Based on the first score and/or second score, the authentication platform can determine whether to authenticate the human speaker as the individual (step 1005). If the authentication platform determines that the human speaker should be authenticated as the individual, additional action(s) may be performed. For example, the authentication platform could notify a payment processor that biometric authentication of the human speaker has been successfully completed. Similarly, additional action(s) may be performed if the authentication platform determines that the human speaker could not be authenticated as the individual. In such a scenario, the authentication platform may request that another phrase be uttered by the human speaker for authentication purposes, or the authentication platform may prevent or inhibit a transaction involving the human speaker from being completed (e.g., by notifying the payment processor that biometric authentication of the human speaker has not been successfully completed).

Unless contrary to physical possibility, it is envisioned that the steps described above may be performed in various sequences and combinations. For example, an authentication platform could simultaneously execute the training phase of an authentication procedure for one individual and the usage phase of an authentication procedure for another individual. As another example, an authentication platform could simultaneously execute multiple instances of an authentication procedure using data associated with the left and right ears. In such embodiments, the same audio data could be used for both ears, though the authentication platform may obtain a first set of shape data for the left ear and a second set of shape data for the right ear.

Other steps may also be included in some embodiments. As an example, assume that an authentication platform causes a first notification to be presented that prompts an individual to utter a phrase while positioning an electronic device proximate to the auricle. For instance, the first notification may request that the individual utter the phrase while the electronic device is positioned in the auricle (e.g., in the case of an earphone), or the first notification may request that the individual utter the phrase while the electronic device is positioned near the auricle (e.g., in the case of a mobile phone). In such a scenario, the authentication platform may opt to increase security by supplementing the authentication procedure with another form of biometric authentication. For example, the authentication platform may cause a second notification to be generated that prompts the individual to place a finger proximate to a fingerprint sensor of the electronic device, in which case the image of the fingerprint can be compared to a relevant biometric database. As another example, the authentication platform may cause a second notification to be generated that prompts the individual to place an eye proximate to the camera of the electronic device, in which case the image of the eye can be compared to a relevant biometric database.

Processing System

Figure 11:
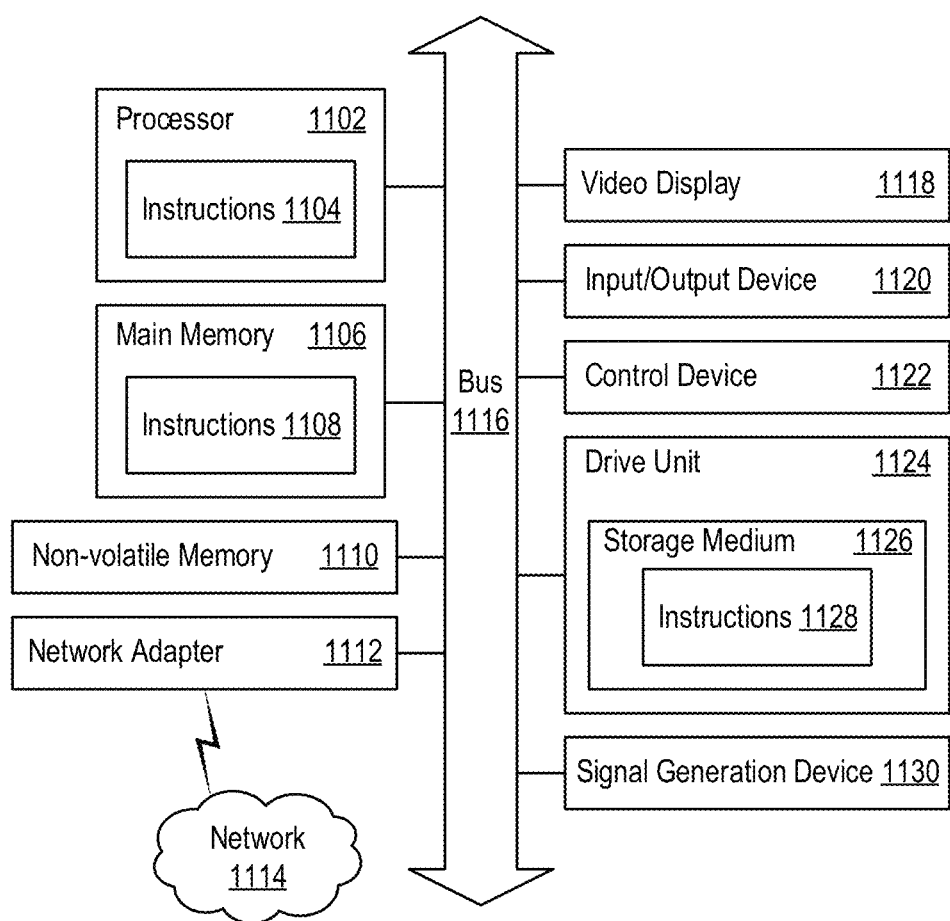
FIG. 11 is a block diagram illustrating an example of a processing system in which at least some operations described herein can be implemented.

FIG. 11 is a block diagram illustrating an example of a processing system 1100 in which at least some operations described herein can be implemented. For example, components of the processing system 1100 may be hosted on an electronic device that includes a microphone (e.g., microphone 204 of FIG. 2A), shape sensor (e.g., shape sensor 206 of FIG. 2A), or processor operable to execute an authentication algorithm (e.g., processor 208 of FIG. 2A). As another example, components of the processing system 1100 may be hosted on an electronic device that includes an authentication platform (e.g., authentication platform 414 of FIG. 4).

The processing system 1100 may include a processor 1102, main memory 1106, non-volatile memory 1110, network adapter 1112 (e.g., a network interface), video display 1118, input/output device 1120, control device 1122 (e.g., a keyboard, pointing device, or mechanical input such as a button), drive unit 1124 that includes a storage medium 1126, or signal generation device 1130 that are communicatively connected to a bus 1116. The bus 1116 is illustrated as an abstraction that represents one or more physical buses and/or point-to-point connections that are connected by appropriate bridges, adapters, or controllers. The bus 1116, therefore, can include a system bus, Peripheral Component Interconnect (PCI) bus, PCI-Express bus, HyperTransport bus, Industry Standard Architecture (ISA) bus, Small Computer System Interface (SCSI) bus, Universal Serial Bus (USB), Inter-Integrated Circuit ($I^2C$) bus, or bus compliant with Institute of Electrical and Electronics Engineers (IEEE) Standard 1394.

The processing system 1100 may share a similar computer processor architecture as that of a computer server, router, desktop computer, tablet computer, mobile phone, video game console, wearable electronic device (e.g., a watch or fitness tracker), network-connected ("smart") device (e.g., a television or home assistant device), augmented or virtual reality system (e.g., a head-mounted display), or another electronic device capable of executing a set of instructions (sequential or otherwise) that specify action(s) to be taken by the processing system 1100.

While the main memory 1106, non-volatile memory 1110, and storage medium 1124 are shown to be a single medium, the terms "storage medium" and "machine-readable medium" should be taken to include a single medium or multiple media that stores one or more sets of instructions 1126. The terms "storage medium" and "machine-readable medium" should also be taken to include any medium that is capable of storing, encoding, or carrying a set of instructions for execution by the processing system 1100.

In general, the routines executed to implement the embodiments of the present disclosure may be implemented as part of an operating system or a specific application, component, program, object, module, or sequence of instructions (collectively referred to as "computer programs"). The computer programs typically comprise one or more instructions (e.g., instructions 1104, 1108, 1128) set at various times in various memories and storage devices in a computing device. When read and executed by the processor 1102, the instructions cause the processing system 1100 to perform operations to execute various aspects of the present disclosure.

While embodiments have been described in the context of fully functioning computing devices, those skilled in the art will appreciate that the various embodiments are capable of being distributed as a program product in a variety of forms. The present disclosure applies regardless of the particular type of machine- or computer-readable medium used to actually cause the distribution. Further examples of machine- and computer-readable media include recordable-type media such as volatile and non-volatile memory devices 1110, removable disks, hard disk drives, optical disks (e.g., Compact Disk Read-Only Memory (CD-ROMS) and Digital Versatile Disks (DVDs)), cloud-based storage, and transmission-type media such as digital and analog communication links.

The network adapter 1112 enables the processing system 1100 to mediate data in a network 1114 with an entity that is external to the processing system 1100 through any communication protocol supported by the processing system 1100 and the external entity. The network adapter 1112 can include a network adaptor card, a wireless network interface card, a switch, a protocol converter, a gateway, a bridge, a hub, a receiver, a repeater, or a transceiver that includes an integrated circuit (e.g., enabling communication over Bluetooth or Wi-Fi).

The techniques introduced here can be implemented using software, firmware, hardware, or a combination of such forms. For example, aspects of the present disclosure may be implemented using special-purpose hardwired (i.e., non-programmable) circuitry in the form of application-specific integrated circuits (ASICs), programmable logic devices (PLDs), field-programmable gate arrays (FPGAs), and the like.

REMARKS

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A non-transitory medium with instructions stored thereon that, when executed by a processor of an electronic device, cause the processor to perform operations comprising:
   acquiring data that is representative of a series of return signals generated by reflection of a series of probing signals that are emitted into an ear canal as an individual utters a phrase as a biometric credential for authentication;
   producing, based on the series of return signals, a model that indicates how a shape of the ear canal varies over time as the phrase is uttered by the individual; and
   storing the model in a profile that is associated with the individual in a biometric database,
      wherein the model is one of multiple models stored in the profile that is associated with the individual, and
      wherein each model of the multiple models is associated with a different phrase.

2. The non-transitory medium of claim 1, wherein the profile is one of multiple profiles stored in the biometric database, and wherein each profile of the multiple profiles is associated with a different individual.

3. The non-transitory medium of claim 1, wherein the operations further comprise:
   causing a notification to be generated that prompts the individual to utter the phrase.

4. The non-transitory medium of claim 3, wherein the individual is prompted to utter the phrase while wearing a second electronic device in an auricle of an ear, and wherein the series of return signals are detected by the second electronic device.

5. The non-transitory medium of claim 3, wherein the notification is visually presented by the electronic device.

6. The non-transitory medium of claim 3, wherein the notification is audibly presented by the electronic device.

7. The non-transitory medium of claim 1, wherein the operations further comprise:
   causing a first notification to be generated that prompts a human speaker in possession of the electronic device to utter the phrase while positioning the electronic device proximate to an auricle of an ear;
   acquiring second data that is representative of a second series of return signals generated by reflection of a second series of probing signals emitted into an ear canal of the human speaker by the electronic device; and
   establishing whether to authenticate the human speaker as the individual based on whether deformation of the ear canal as the phrase was uttered as inferred from the second data matches the model that indicates how the ear canal deforms as the phrase is uttered by the individual.

8. The non-transitory medium of claim 1, wherein the model includes a series of discrete positions that indicate deformation of the ear canal at corresponding points in time.

9. The non-transitory medium of claim 1, wherein a frequency of the series of probing series emitted into the ear canal changes over time.

10. The non-transitory medium of claim 7, wherein the operations further comprise:
    causing a second notification to be generated that prompts the human speaker to place a finger proximate to a fingerprint sensor of the electronic device;
    acquiring an image of a fingerprint that was generated by the fingerprint sensor; and
    causing the image to be compared to a second biometric database to determine whether a matching entry is found.

11. The non-transitory medium of claim 10, wherein said establishing is based on (i) deformation of the ear canal as inferred from the second data and (ii) the matching entry in the second biometric database.

12. The non-transitory medium of claim 7, wherein the operations further comprise:
    causing a second notification to be generated that prompts the human speaker to place an eye proximate to a camera of the electronic device;
    acquiring an image of the eye that was generated by the camera; and
    causing the image to be compared to a second biometric database to determine whether a matching entry is found.

13. The non-transitory medium of claim 12, wherein said establishing is based on (i) deformation of the ear canal as inferred from the second data and (ii) the matching entry in the second biometric database.

* * * * *